United States Patent [19]

Mayled

[11] Patent Number: 5,152,397

[45] Date of Patent: Oct. 6, 1992

[54] COMBINATION HOLDER AND CONTAINER

[76] Inventor: Edward C. Mayled, 28 Groveland Crescent, Brampton, Ontario, Canada, L6S 1L2

[21] Appl. No.: 725,824

[22] Filed: Jul. 3, 1991

[51] Int. Cl.⁵ .............................................. B65D 73/00
[52] U.S. Cl. ............................... 206/486; 53/471; 206/0.5; 206/806; 239/57; 239/60
[58] Field of Search .................. 53/467, 471; 206/0.5, 206/486, 488, 489, 524.1, 806; 239/55, 57-60

[56] References Cited

U.S. PATENT DOCUMENTS

| | | | |
|---|---|---|---|
| 1,552,082 | 9/1925 | Riley | 239/60 |
| 2,738,225 | 3/1956 | Meek | 239/60 |
| 2,765,194 | 10/1956 | Will | 239/60 |
| 2,809,863 | 10/1957 | Curran | 239/60 |
| 2,896,853 | 7/1959 | Curran | 239/60 |
| 3,370,733 | 2/1968 | Giesler | 206/806 |
| 3,521,816 | 7/1970 | Wilson | 239/60 |

FOREIGN PATENT DOCUMENTS 1012272  7/1952  France .................. 239/57

*Primary Examiner*—Jimmy G. Foster
*Attorney, Agent, or Firm*—Samuel Meerkreebs

[57] ABSTRACT

A water charcoal filter is recycled by removing the exhausted charcoal from the plastics container forming the charcoal filter and replacing it with a solid vaporizing substance such as mothballs or a deodorizing substance, closing the lid on the container and placing the lid and body of the container in a holder such as a sheet with cutouts therein. One of the cutouts conforms to the outline of the container while the other cutout is in the form of a hanger.

5 Claims, 2 Drawing Sheets

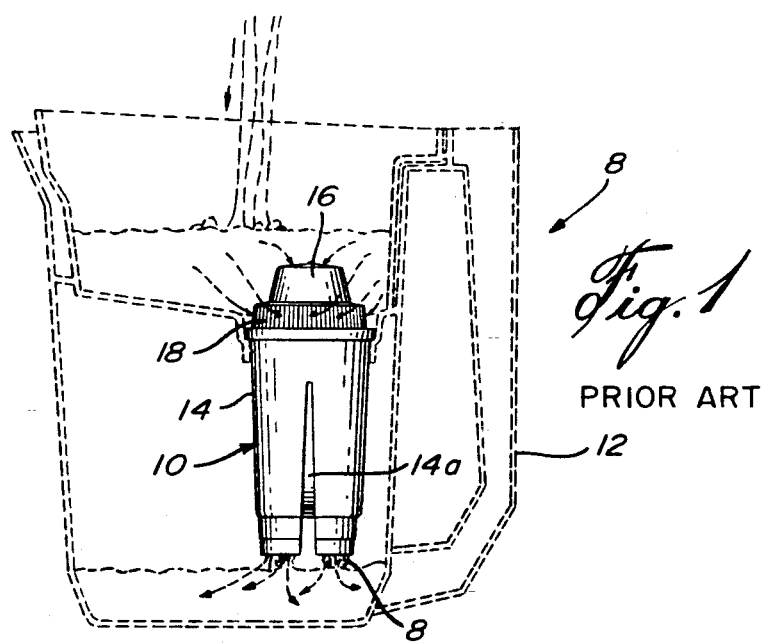
Fig. 1 PRIOR ART
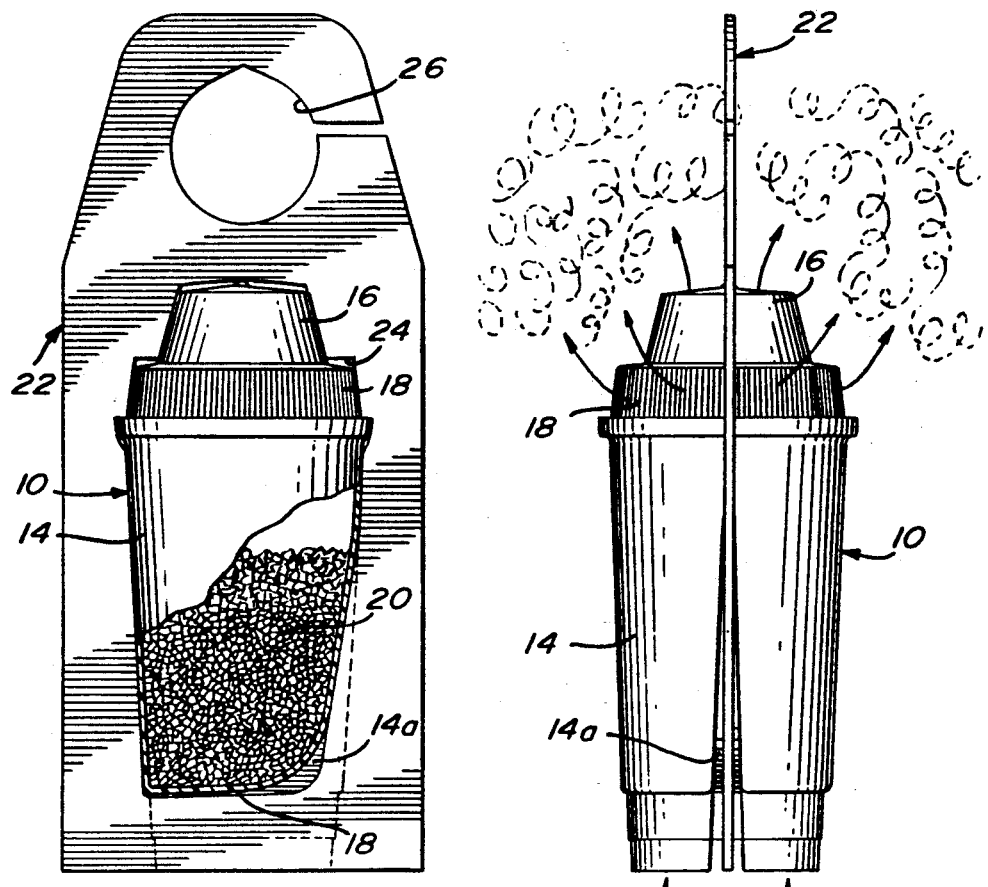
Fig. 2
Fig. 3

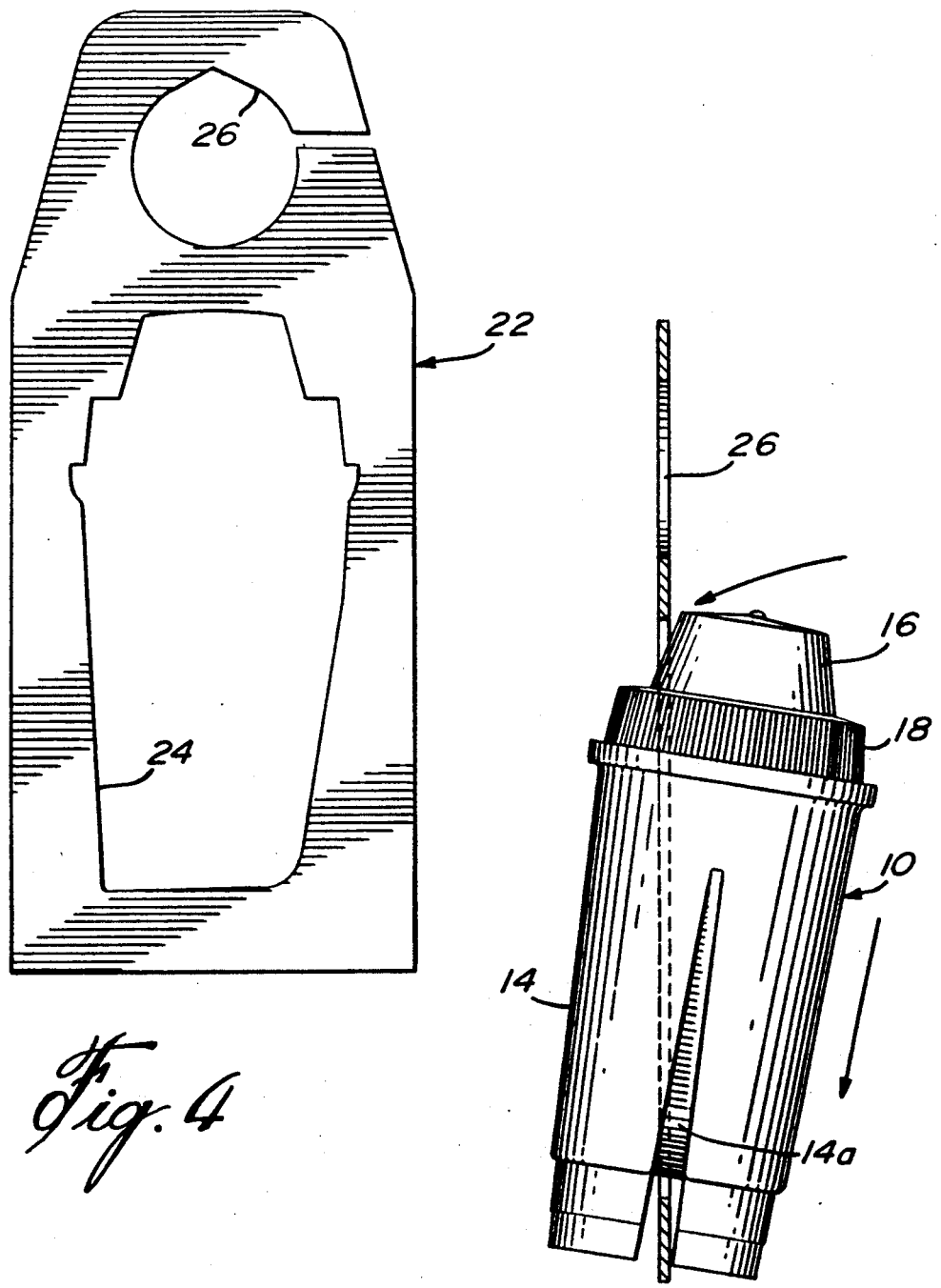

COMBINATION HOLDER AND CONTAINER

BACKGROUND OF THE INVENTION

1. Field of the Invention

The present invention relates to a method of recycling a charcoal water filter container and to a holder and container combination for supporting solid vaporizing substances or the like.

2. Description of the Prior Art

At least one company, Brita Wasserfilter GmbH, produces a plastic disposable water filter container and this under the trade-mark BRITA. The BRITA container includes a hollow body and lid, with openings in both the body and lid. The purpose of the container is to hold the granulated charcoal which is an essential part of the water filter. The openings in the lid and body are provided to allow the water to flow through the filter. The lid is usually sealed to the body by ultrasonic welding. When the usefulness of the charcoal as a filter is expended, the container and charcoal package are disposed of, usually in the garbage. Several other water filter manufacturers supply similar disposable containers.

Such a disposable product merely adds to the enormous problems faced by municipal governments around the world in respect of waste disposal. Statistics show that over 5,000,000 BRITA filters have been dumped in the Province of Ontario, Canada, alone.

SUMMARY OF THE INVENTION

It is an aim of the present invention to propose a new use for this type of water filter container which would otherwise add to existing waste disposal problems.

A further aim of the present invention is to provide a holder, in combination with the recycled water filter container, to recycle it into a vaporizer device or the like.

A further aim of the present invention is to provide a holder which can be used to hang the recycled container in a suitable location, such as a kitchen or bathroom where deodorizing vapors emitting from the dispenser might be required. Likewise, mothballs could be contained within the recycled container and hung in a clothes storage area, such as a cedar closet.

A device for supporting a solid vaporizing substance according to the present invention comprises in combination a recycled container and a holder for maintaining the container in a closed condition and supported. The recycled container comprises a hollow plastics body open at one end and a lid to close the open end, the body and the lid having discrete openings located in predetermined locations such that air can circulate through the container with little resistance. The holder has a container retaining portion and a support portion integrated with the container retaining portion such that the container retaining portion has means to intimately engage a portion of the body and lid to retain the lid in a closed position on the body without obstructing the normal flow of air through the discrete openings in the body and lid. The support portion has means for supporting the holder and the container on a suitable support member without impeding the normal flow of air through the container.

In a more specific embodiment of the present invention, the recycled container is a plastics charcoal filter container from which the charcoal has been removed and replaced by a solid vaporizing substance.

A method of reusing a charcoal water filter container is provided, wherein the container is a hollow plastic body and lid having discrete openings for the passage of water through the container, including the steps of removing the lid from the body and emptying the charcoal material, adding a solid vaporizing substance in the body of the container, replacing the lid on the body and applying a holder to the container in a manner to retain the lid on the body and to support the container on a support member without obstructing the normal passage of air through the discrete openings in the container.

It is also contemplated that the container can be recycled as a toy, for instance the holder 22 can be cut in any shape such as the shape of a rocket or other toy shape and one can imagine toy soldiers being placed inside the container as in a space transporter. The container can be considered again in the toy environment, as a capsule to be carried by a rocket or other space or land vehicles. Thus in the broadest concept of the present invention there is provided a recycled container and a holder for maintaining the container in a closed condition and supported. The recycled container comprises a hollow plastics body opened at one end and a lid to close the open end. The holder has a container retaining portion and a support portion integrated with the container retaining portion such that the container retaining portion has means to intimately engage a portion of the body and lid to retain the lid in closed position on the body. The support portion has means for supporting this holder and the container on a suitable support member.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 is a front elevation of a charcoal filter shown in a water filtering environment;

FIG. 2 is a front elevation, partly in cross-section, of the recycled charcoal filter container in combination with a holder in accordance with the present invention;

FIG. 3 is a side elevation thereof;

FIG. 4 is a front elevation of the holder; and

FIG. 5 is a side elevation with the holder partly in cross-section, showing the container being fitted therein.

DESCRIPTION OF THE PREFERRED EMBODIMENTS

The charcoal filter 8, as shown in FIG. 1, is the BRITA water filter including a container shown in a water pitcher 12 illustrated in dotted lines. As shown, the charcoal filter container 10 has a body 14 with a lid 16.

Openings 18 are provided in the lid 16 and in the bottom of the body 14. The lid 16 is normally ultrasonically welded to the body 14.

In its normal use, the container 10 is filled with charcoal particles and is located in a special seat in a pitcher 12. Water is poured into the upper portion of the pitcher 12 and forced to pass through the openings 18 in the lid 16 and thus through the charcoal within the container 10 and out the openings 18 in the bottom of the body 14.

When the charcoal is exhausted, the container 10 is removed and thrown away.

In an attempt to recycle the plastic container 10, once the charcoal has been exhausted, the lid 16 is pried from the body 14 and filled with a solid vaporizing substance 20, as illustrated in FIG. 2. This vaporizing substance 20 could be mothballs or a solid deodorizing substance which allows a neutralizing odor or a fragrance to be emitted from the container 10. Lavender petals, wild flower leaves and other similar fragrance emitting substances may be used. The openings 18 in the lid 16 and in the body 14 of the container are satisfactory to allow air to pass through the container 10 and vapors to be emitted.

One of the problems encountered with recycling the charcoal container 10 is to retain the lid 16 on the body 14. When the lid 16 and the body 14 are assembled for the purpose of the charcoal filter, ultrasonic welding is used, and the lid must be pried physically from the body 14 when recycling the container. It is not possible to replace the lid 16 on the body 14 in a manner wherein the lid 16 will stay fixed to the body 14. Thus, a planar holder member 22 made preferably of paperboard sheet material is provided having a cutout 24 which conforms to the outline of the container 10. By pressing the assembled container 10 into the cutout portion 24, the lid 16 is retained on the body 14. In the present BRITA model charcoal filter as illustrated in FIG. 1, a groove 14a is provided on one portion of the surface of the body 14 which allows the cardboard holder 22 to nest therein.

The other purpose of the holder 22 is to support the recycled container 10 in a required location. Preferably, a cutout 26 is provided in the form of a hanger such that the holder 22 can be hung on a hook in a bathroom or kitchen. The hanger 26 can be used for hanging the holder and container on a towel rack or similar support member. Likewise, if the container 10 contains mothballs and is to be used in a closet or cedar closet, the hanger 26 could be adapted to be hung on a clothes rail within the closet.

The holder 22 can take any form as long as it is sufficiently unobstrusive to the discrete openings 18 in order not to block the normal flow of air and vapors from passing through the openings 18. The holder 22 could be made to be supported on a support surface rather than to be hung.

The result, of course, is that the charcoal filter 10, which is normally thrown away, can be recycled and reutilized indefinitely by replacing the solid vaporizing substance 20 within the container.

FIG. 4 shows the holder 22 with the cutout 24 and the hanger 26.

FIG. 5 shows the container 10 having a body 14 and a lid 16 in place and being inserted into the holder 22.

I claim:

1. A device for supporting a solid vaporizing substance comprising, in combination, a recycled container and a holder for maintaining the container in a closed condition and supported, the recycled container comprising a hollow plastics body open at one end and a lid to close the open end, the body and the lid having discrete openings located in predetermined locations such that air can circulate through the container with little resistance, the holder having a container retaining portion and a support portion integral with the container retaining portion, wherein the holder is in the form of a paperboard sheet material having a cutout conformed to the outline of the container so as to retain the lid on the container and a hanger is defined in the support portion of the holder, the hanger being in the form of a cutout hook, the holder engages the body without obstructing the normal flow of air through the discrete openings in the body and lid and the support portion has means for supporting the holder and container on a suitable support member without impeding the normal flow of air through the container.

2. A device as defined in claim 1, wherein the recycled container is a plastics charcoal water filter container from which the charcoal has been removed and replaced by a solid vaporizing substance.

3. A recycled container as defined in claim 1, wherein the solid vaporizing material is mothballs.

4. A recycled container as defined in claim 1, wherein the solid vaporizing substance is a deodorizing substance.

5. A method of reusing a charcoal water filter container, wherein the container is a hollow plastics body and with a lid having discrete openings for the passage of water through the container, including the steps of removing the lid from the body and disposing of the charcoal material, adding a solid vaporizing substance in the body of the container, replacing the lid on the body and applying a holder to the container in a manner to retain the lid on the body and to support the container on a support member without obstructing the normal passage of air through the discrete openings in the container.

* * * * *